US008436071B2

(12) United States Patent
Hatton et al.

(10) Patent No.: US 8,436,071 B2
(45) Date of Patent: May 7, 2013

(54) DENTAL REPAIR MATERIAL (75) Inventors: John F. Hatton, Saint Louis, MO (US);
Benjamin S. Ber, Houma, LA (US);
Gregory P. Stewart, Edwardsville, IL (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 13/251,574

(22) Filed: Oct. 3, 2011

(65) Prior Publication Data

US 2012/0073469 A1 Mar. 29, 2012

Related U.S. Application Data (62) Division of application No. 11/473,536, filed on Jun. 23, 2006, now abandoned.

(60) Provisional application No. 60/693,268, filed on Jun. 23, 2005.

(51) Int. Cl.
*A61L 24/08* (2006.01)
*A61K 6/06* (2006.01)
*A61K 6/097* (2006.01)

(52) U.S. Cl.
USPC ........... 523/116; 523/113; 523/115; 523/117; 433/226; 433/228.1

(58) Field of Classification Search ................... 523/116, 523/113, 115, 117; 433/226, 228.1
See application file for complete search history.

(56) References Cited

U.S. PATENT DOCUMENTS

| 4,647,600 A * | 3/1987 | Kawahara et al. ............ 523/116 |
| 5,415,547 A * | 5/1995 | Torabinejad et al. ...... 433/228.1 |
| 5,769,638 A * | 6/1998 | Torabinejad et al. ...... 433/228.1 |
| 2003/0159618 A1* | 8/2003 | Primus ........................... 106/35 |

FOREIGN PATENT DOCUMENTS

SU 1411439 A1 * 7/1986
SU 1361305 A1 * 12/1987

OTHER PUBLICATIONS

Derwent English abstract of Natsibulin et al. (SU 1361305); 1988.*
English language abstract of Ashrafyan et al. (SU 11411439); Apr. 6, 2011.*

* cited by examiner

*Primary Examiner* — Michael Pepitone
(74) *Attorney, Agent, or Firm* — Armstrong Teasdale LLP (57) ABSTRACT The invention is directed to an improved dental composition useful in the repair of cavities, apex repairs, root perforations and root canals. Disclosed is a dental composition and dental composition additive which have improved handling characteristics, for example improved viscosity and setting time. The addition of effective amounts of a modified cellulose and calcium chloride to available dental repair compounds, such as mineral trioxide compound, results in the improved dental composition without affecting the other characteristics of the dental repair compound.

17 Claims, 8 Drawing Sheets

DENTAL REPAIR MATERIAL

CROSS-REFERENCE TO RELATED APPLICATIONS

This application is a divisional application of U.S. patent application Ser. No. 11/473,536, filed Jun. 23, 2006 and now abandoned, which claims priority to Provisional U.S. Patent Application No. 60/693,268, which was filed on Jun. 23, 2005, both of which are incorporated by reference in their entireties.

BACKGROUND OF THE INVENTION

1. Field of the Invention

The invention is related to dental repair materials. Specifically improved MTA (mineral trioxide aggregate) with improved handling and sealing properties.

2. Summary of the Related Art

Various compounds have been used as dental fill materials for cavities and root canal therapy. These include Amalgam, Reinforced Zinc Oxide-Eugenol (IRM and Super EBA), Composite Resins and Mineral Trioxide Aggregate (MTA) and Portland Cement, herein after referred to generally as "Dental Repair Compound".

The attributes generally sought for root-end filling material include the ability to 1) seal the apical portion in three dimensions, 2) be well tolerated by the periradicular tissues with no inflammatory reactions, 3) be non-toxic, 4) not promote, and preferably inhibit, the growth of pathogenic organisms, 5) stimulate the regeneration of normal repiradicular tissues, 6) not be affected by moisture in either the set or unset state, 7) not be absorbable by the body within the confines of the tooth, but excess should be absorbable, 8) be dimensionally stable and should not expand, contract, or flow in any direction when set, 9) not corrode or be electrochemically active, 10) not stain the tooth or the periradicular tissues, 11) be easy to mix and insert, 12) be easily distinguishable on radiographs, and 13) adhere or bond to the tooth without the need of undercuts.

MTA has been demonstrated to have diverse applications for all fields of dentistry and appears to fulfill most characteristics of an ideal cement due to its unique properties such as tissue compatibility, marginal adaptation, sealing ability, hydrophilic properties, and the capacity to stimulate hard tissue formation. These properties have allowed MTA to be indicated for the following endodontic procedures: Pulp Capping, Apexification, Perforation repair and other Miscellaneous uses.

Pulp Capping—In 1929, Hess reported a pulpotomy technique using calcium hydroxide. Until recently, these calcium hydroxide-based materials have found widespread use in traditional vital pulp therapy and have been the mainstay for the protection of exposed dental pulps. The healing process of the dental pulp following a pulpotomy or a direct pulp cap is characterized by the formation of a hard tissue bridge with the maintenance of a vital subjacent pulp tissue free from chronic inflammatory cells. Recently, MTA has been approved by the FDA and recommended for direct pulp capping. MTA's mechanism of action is thought to be similar to that of calcium hydroxide. MTA has calcium oxide that mixes with water to form calcium hydroxide. The reaction of the calcium from the calcium hydroxide with the carbon dioxide from the pulp tissue produces calcite crystals. These calcite crystals are thought to be the initiating factor in the induction of a hard tissue barrier. Seux (1) observed a rich extracellular network of fibronectin in close contact with these crystals and concluded that both were integral in the initiating steps in the formation of a hard tissue barrier. Tziafas (2) concluded that MTA was able to induce cytological and functional changes in pulpal cells, resulting in the formation of fibrodentin at the surface of a mechanically exposed dental pulp.

Human studies have shown MTA to cause less pulpal hyperemia, inflammation, and necrosis when compared to calcium hydroxide. In a study performed by Aeinehchi, (7) MTA induced a thicker dentinal bridge in third molars and was found to be associated with an intact odontoblastic layer more often than with calcium hydroxide. Additional reasons MTA is an effective pulp capping material is its ability to effectively seal the dentin-material interface to prevent bacterial contamination, it is nonresorbable, proven biocompatibility, and beneficial alkaline properties (25; 26; 27). Because of this, MTA is also recommended for treatment of traumatically exposed pulps for the treatment of complicated crown fractures (8).

Apexification—The traditional protocol in the treatment of necrotic immature teeth is through apexification using calcium hydroxide. In 1959, Granath was the first to describe the utilization of calcium hydroxide for apical closure. In 1966, Frank mainstreamed the apexification technique and was credited as being the first to use this modality (9). This methodology consists of multiple appointments exchanging calcium hydroxide as the intracanal medicament to induce an apical hard tissue barrier ultimately to control the root canal filling material. The calcium hydroxide is changed every 3 months until there is evidence of apical barrier formation. The most important problem with the classic apexification technique with calcium hydroxide is the duration of therapy, which can last from 3 to 24 months (9; 10). During this time frame the root canal is susceptible to reinfection due to the difficulty in maintaining a temporary restorative material that adequately seals the access opening. The root is also at risk to fracture due to the long treatment time required for apical barrier formation.

MTA treatment of these cases allows for a single treatment of immature teeth as an option. The MTA apical plug technique, a one-step obturation after short canal disinfection with calcium hydroxide is designated to create an artificial stop to the filling material. The physical characteristics of MTA provide advantages over the traditional calcium hydroxide technique. MTA apexification cases can be restored in approximately two weeks as opposed to traditional calcium hydroxide therapy, which could take several months. MTA provides excellent marginal adaptation to prevent leakage and the material is non-resorbable. In 1996, Buchanan first recommended the use of MTA for one-appointment apexification by placing an apical matrix of freeze-dried demineralized bone followed by condensation of MTA (11). Witherspoon also recommends a technique for one-visit apexification. This technique advocates filling the apical to middle third with MTA, with the remainder of the canal system to be restored with a core material to reinforce the thin walls of the root (12). Giuliani described using MTA as an apical plug in teeth with necrotic pulps and open apices. His technique advocated the use of calcium hydroxide treatment for one week prior to placement of MTA as an apical plug with subsequent obturation of the canal system. At recall, the clinical symptoms and teeth with periapical lesions had resolution within 6-12 months (13). Hachmeister, in an MTA displacement study, concluded there was a significant greater resistance to force with a 4 mm thickness of MTA, regardless of calcium hydroxide use. Thus, the ideal recommended thickness of the apical plug was shown to be 4 mm, in order to resist displacement of the material (14).

Perforation Repair—In dentistry, procedural accidents such as root or furcal perforations can occur during root canal therapy, post space preparation, or as a consequence of internal resorption. Studies have shown that these perforations predispose periradicular tissues to chronic inflammation and promote the advancement of periodontal attachment loss, ultimately causing the loss of the tooth (15). Ingle reported that perforations were the second greatest cause of endodontic failure and accounted for 9.6% of all unsuccessful cases (16).

The repair of perforations can be problematic due to extrusion of the repair filling material, improper hemorrhage control, and the ability of the material to adequately seal the perforation site. MTA's unique physical characteristics allowing for superior marginal adaptation and sealing ability in hematic environments along with its osteo/cementoconductive attributes make it an excellent material for perforation repair (28; 29; 30; 31). The inherent hydrophilic properties of MTA allow the repair material to set in a wet environment and adequately seal the perforation site. In 1993, Lee reported the first in vitro study investigating the sealing ability of MTA for repair of lateral root perforations. The authors were able to demonstrate that moisture of the surrounding tissue acted as an activator of the chemical reaction and did not pose a risk with its use in a moist environment. They were also able to demonstrate that overextrusion of the material into the perforation site occurred mostly in the IRM group, followed by the amalgam group and then MTA. Lee concluded that the hydrophilic powder absorbs moisture and allows for minimal condensation force, thus decreasing the chance of overextrusion of the material (49). Sluyk concluded that the presence of moisture in the perforation site during placement was advantageous in aiding adaptation of MTA to the walls of the perforation (86).

Histologic repair of the perforation is possible with MTA. Pitt Ford et al. demonstrated using an in vitro canine model, that cementum has been was produced over MTA repairing perforations in the absence of inflammation. Based on these results, Pitt Ford recommended the use of MTA for immediate perforation repair (19). Holland also demonstrated no inflammation associated with repair of lateral root perforations with MTA over a 180 day observation period and that there was evidence of cementum deposition in the majority of specimens (20). Recent studies performed to evaluate the clinical efficacy of MTA to seal both furcal and lateral perforations have only validated MTA as the material of choice in perforation repair (88-90).

Miscellaneous Uses—Additional uses for MTA have also been suggested. In a study performed by Cummings, MTA was compared to other materials and evaluated as an isolating barrier for internal bleaching. MTA demonstrated the least amount of leakage compared to IRM and zinc phosphate. It was concluded that this material can be used as an effective isolating barrier for internal bleaching (21).

There have been several case reports documenting alternative uses for MTA. Hsiang-Chi presented a successful case report demonstrating the repair of perforating internal resorption with MTA. A partial pulpotomy was performed, and the material was placed adjacent to the exposed pulp. Teeth were extracted after 6 months. Histological exam of the teeth showed continuous dentin bridge formation without inflammation 6 months after initial treatment (93). O'Sullivan (23), in another case report, demonstrated obturation of the canal system with MTA in a retained primary mandibular second molar where there was no succendaneous tooth present. Eidelman et al. found clinical and radiographic success as a dressing material following pulpotomy in primary teeth, suggesting MTA as a possible alternative to formocresol in primary teeth (24).

Presently, dental materials, such as e.g., MTA, Portland cement, are difficult to handle due to viscosity and slow setting times. These materials have low viscosity and therefore require special equipment to administer into small or tortuous areas in the patient's mouth.

U.S. Pat. Nos. 5,415,547, and 5,769,638 titled "Tooth Filling Material and Method of Use." Teach the use of Portland Cement as a dental repair material for apicoectomy, a tooth cavity, correction of root perforation. Those patents also teach a method of performing a apicoectomy, a method for filling teeth and a method for sealing root perforations. It has also been observed that Portland Cement has similar properties to MTA as a dental repair compound.

International Patent Application WO 2005/039509 A1, titled "A Dental Composite Material and Uses Thereof" Teaches using a viscosity enhancing additive in Portland Cement. The application also teaches using the same viscosity enhancing substance to improve MTA as a workable dental repair material. However the description suggested enhancement of MTA. The viscosity enhancing substance is Polyvinyl alcohol, cellulose, cellulose derivatives, polyethylene oxide, natural gums, and/or aqueous clay dispersion.

The following references are cited throughout this section using the related parenthetical numbering system. The references are incorporated herein by reference. Applicant reserves the right to challenge the veracity of statements made therein.

1) Seux D, Regad C, Magloire H, Holz J. A model of an in vitro biological assay controlled by immunofluorescence and scanning electron microscopy. J Biol Buccale. 1991; 19:147-53.
2) Tziafas D, Pantelidou O, Alvanou A, Belibasakis G, Papadimitriou S. The dentinogenic effect of mineral trioxide aggregate (MTA) in short-term capping experiments. Int Endod J 2002; 35:245-54.
3) Pitt Ford T R, Torabinejad M, Abedi H R, Bakland L K, Kariyawasam S P. Using mineral trioxide aggregate as a pulp-capping material. J Am Dent Assoc 1996; 127:1491-4.
4) Faraco I M, Jr., Holland R. Response of the pulp of dogs to capping with mineral trioxide aggregate or a calcium hydroxide cement. Dent Traumatol 2001; 17:163-6.
5) Junn D J, McMillan P, Bakland L K, Torabinejad M. Quantitative assessment of dentin bridge formation following pulp capping with Mineral Trioxide Aggregate (MTA).[Abstract #29] J Endod 1998; 24:278.
6) Dominguez M S, Witherspoon D E, Gutmann J L, Opperman L A. Histological and scanning electron microscopy assessment of various vital pulp-therapy materials. J Endod 2003; 29:324-33.
7) Aeinehchi M, Eslami B, Ghanbariha M, Saffar A S. Mineral trioxide aggregate (MTA) and calcium hydroxide as pulp-capping agents in human teeth: a preliminary report. Int Endod J 2003; 36:225-31.
8) Bakland L K. Management of traumatically injured pulps in immature teeth using MTA. J Calif Dent Assoc 2000; 28:855-8.
9) Frank A. Therapy for the divergent pulpless tooth by continued apical formation. J Am Dent Assoc 1966; 72:87-93.
11) Buchanan L S. One-visit endodontics: a new model of reality. Dent Today 1996; 15:36, 8, 40-3.
12) Witherspoon D E, Ham K. One-visit apexification: technique for inducing root-end barrier formation in apical closures. Pract Proced Aesthet Dent 2001; 13:455-60.

13) Giuliani V, Baccetti T, Pace R, Pagavino G. The use of MTA in teeth with necrotic pulps and open apices. Dent Traumatol 2002; 1 8:217-21.
14) Hachmeister D R, Schindler W G, Walker W A, 3rd, Thomas D D. The sealing ability and retention characteristics of mineral trioxide aggregate in a model of apexification. J Endod 2002; 28:386-90.
15) Seltzer S, Sinai I, August D. Periodontal effects of root perforations before and during endodontic procedures. J Dent Res. 1970; 49:332-9.
16) Ingle J I. A standardized endodontic technique utilizing newly designed instruments and filling materials. Oral Surg Oral Med Oral Pathol. 1961; 14:83-91.
17) Lee S J, Monsef M, Torabinejad M. Sealing ability of a mineral trioxide aggregate for repair of lateral root perforations. J Endod 1993; 19:541-4.
18) Sluyk S R, Moon P C, Hartwell G R. Evaluation of setting properties and retention characteristics of mineral trioxide aggregate when used as a furcation perforation repair material. J Endod. 1998; 24:768-71.
19) Pitt Ford T R, Andreasen J O, Dorn S O, Kariyawasam S P. Effect of various zinc oxide materials as root-end fillings on healing after replantation. Int Endod J 1995; 28:273-8.
20) Holland R, Filho J A, de Souza V, Nery M J, Bemabe P F, Junior E D. Mineral trioxide aggregate repair of lateral root perforations. J Endod. 2001; 27:281-4.
21) Cummings G R, Torabinajad M. Mineral Trioxide Aggregate (MTA) as an isolating barrier for internal bleaching. [Abstract #53] J Endod. 1995; 21:228.
22) Hsieng H C, Cheng Y A, Lee Y L, Lan W H, Lin C P. Repair of perforating internal resorption with mineral trioxide aggregate: a case report. J Endod. 2003; 29:538-9.
23) O'Sullivan S M, Hartwell G R. Obturation of a retained primary mandibular second molar using mineral trioxide aggregate: a case report. J Endod. 2001; 27:703-5.
24) Eidelman E, Holan G, Fuks A B. Mineral trioxide aggregate vs. formocresol in pulpotomized primary molars: a preliminary report. Pediatr Dent. 2001; 23:15-8.
25) Torabinejad M, Watson T F, Pitt Ford T R. Sealing ability of a mineral trioxide aggregate when used as a root end filling material. J Endod. 1993; 19:591-5.
26) Torabinejad M, Pitt Ford T R, McKendry D J, Abedi H R, Miller D A, Kariyawasam S P. Histologic assessment of mineral trioxide aggregate as a root-end filling in monkeys. J Endod 1997; 23:225-8.
27) Torabinejad M, Hong C U, McDonald F, Pitt Ford T R. Physical and chemical properties of a new root-end filling material. J Endod 1995; 21:349-53.
28) Pitt Ford T R, Torabinejad M, McKendry D J, Hong C U, Kariyawasam S P. Use of mineral trioxide aggregate for repair of furcal perforations. Oral Surg Oral Med Oral Pathol Oral Radiol Endod 1995; 79:756-63.
29) Koh E T, Torabinejad M, Pitt Ford T R, Brady K, McDonald F. Mineral trioxide aggregate stimulates a biological response in human osteoblasts. J Biomed Mater Res. 1997; 37:432-9.
30) Moretton T R, Brown C E, Jr., Legan J J, Kafrawy A H. Tissue reactions after subcutaneous and intraosseous implantation of mineral trioxide aggregate and ethoxybenzoic acid cement. J Biomed Mater Res 2000; 52:528-33.
31) Thompson T S, Berry J E, Somerman M J, Kirkwood K L. Cementoblasts maintain expression of osteocalcin in the presence of mineral trioxide aggregate. J Endod 2003; 29:407-12.

SUMMARY OF THE INVENTION

The inventors have made the surprising discovery that the addition of divalent-cationic halogen salt and derivatives of cellulose polymers to dental repair compounds results in dental repair compositions having improved handling properties, which enables more effective treatment of various indications of use. Those improved handling properties include increased viscosity and shortened setting time. Thus, the invention is directed to compositions, treatment methods, and manufacturing processes for improved dental repair compositions and dental repair procedures.

In one embodiment, the invention is drawn to a dental repair composition, comprising a dental repair compound, such as for example but not limited to Portland cement and mineral trioxide aggregate ("MTA"), a divalent cation halogen salt (e.g., calcium chloride, magnesium chloride, and the like), and a polymer thickening agent, such as a cellulose derivative polymer like methyl-cellulose or the like. In a preferred aspect, the divalent cation halogen salt is calcium chloride and the polymer thickening agent is methyl-cellulose. However, the inventors envision that other salts and polymers, which have similar properties to $CaCl_2$ and methyl-cellulose, may also be used as additives to the dental repair compounds to produce the same improved handling properties (supra). Concentration ranges for the divalent cation halogen salt can be from as low as 0.1% by weight to as high as 20% by weight. Likewise, the concentration range for the polymer thickener can be from as low as 0.1% by weight to as high as 20% by weight. In a more preferred embodiment, the salt is $CaCl_2$ at a concentration of approximately 2% by weight and the polymer thickener is methyl-cellulose at a concentration of approximately 1%. However, the inventors envision that the relative amounts of $CaCl_2$ and methyl-cellulose may be altered outside of these ranges and values, so long as the therapeutic properties of the dental repair compound are not significantly compromised.

In another embodiment, the invention is drawn to a compound additive, which can be added to a dental repair compound (supra). The compound additive is a gel or solution that consists essentially of the divalent cation halogen salt and polymer thickening agent. To produce the improved dental repair composition, the practitioner would mix the compound additive with the dental repair compound to produce the working improved dental repair composition prior to application to the patient. Preferably, the compound additive consists essentially of $CaCl_2$ and methyl-cellulose, both of which are represented at concentrations higher than their respective final concentrations in the working improved dental repair composition.

In another embodiment, the invention is drawn to methods of producing the improved dental repair composition and compound additives (supra). In one particular preferred aspect, calcium chloride is weighed out in an amount representing approximately 2% of the final composition weight. The calcium chloride is added to water for a 3:1 powder to water ratio (by weight). The solution can be divided in half, half of which is heated to 80° C. The methyl-cellulose is weighed out in an amount representing approximately 1% or 2% of the final composition weight. The methyl-cellulose is added to the half of the calcium chloride solution that was heated to 80° C. To this mixture, the other half of the calcium chloride solution (at room temperature) is added to the warm solution and stirred until all of the solid material is in solution. This mixture is then chilled to 0° C. to allow the mixture to thicken. The solution is stirred for about 30 minutes to produce a homogeneous gel. This gel is a compound additive, which may then be added to the dental repair compound (e.g., MTA, Portland cement) to produce the improved dental repair composition.

In another embodiment, the invention is drawn to methods of effecting dental repairs using the improved dental repair compositions described (supra). Those dental repairs include but are not limited to filling a tooth cavity, treating tooth decay, performing root canal therapy, apicoectomy, and sealing a root perforation.

In yet another embodiment, the invention is drawn to a kit useful in the practice of dental repair, said kit comprising a packaged dental repair compound (e.g., Portland cement, MTA), a packaged compound additive (supra), and a set of instructions describing how to mix (e.g., in what proportions) the dental repair compound and compound additive.

DETAILED DESCRIPTION

The following example discloses a single preferred embodiment of the invention. It is meant merely to illustrate the invention and not to limit the invention. The skilled artisan in the practice of this invention will readily recognize that substitutions and alterations can be made while remaining within the metes and bounds of the invention, which are set forth in the claims that follow.

Recently, the inventors herein demonstrate improved characteristics of MTA (PROROOT Dentsply Tulsa Dental, Tulsa, Okla.) through the addition of 1% methylcellulose (MC) and 2% calcium chloride ($CaCl_2$) into its parent cement. The inventors observed that the handling characteristics were vastly improved while the compressive strength of MTA with the additives was not significantly affected and the setting time of MTA with the additives was significantly shorter than the MTA control. This observation also brought about questions on whether the chemical additives have significantly altered any inherent physical properties crucial to MTA's success as an ideal dental cement. Therefore, this example describes the physical properties, (marginal leakage, chemical shrinkage, cement solubility, and washout resistance) of chemically modified MTA (1% MC+2% $CaCl_2$ in MTA/$H_2O$) and compare it to unaltered MTA.

Four different tests were designed and employed to assess marginal leakage, chemical shrinkage, cement solubility, and washout resistance between the unaltered MTA and chemically modified MTA (CMMTA) to ensure that the added chemicals have not deteriorated the aforementioned properties of MTA.

Dye leakage results demonstrated no significant difference between CMMTA and MTA samples. In addition, there was significantly less leakage between the CMMTA and MTA groups compared to amalgam. Chemical shrinkage results reported no significant difference between any of the groups (1-6) at any of the designated timeframes ($T_1$, $T_2$, $T_3$, $T_{24}$, and $T_w$). More importantly, there was no significant difference in mean chemical shrinkage between CMMTA and MTA samples at any of the designated time intervals of the specimens. Cement solubility results revealed no significant difference between CMMTA and MTA groups. Furthermore, results demonstrated no significant difference between weights of the test materials at any designated time intervals ($T_1$, $T_7$, $T_{21}$). Modified washout tests indicated a significant difference observed between groups 1-3. However, there were no significant differences noted between CMMTA and MTA groups.

In conclusion, the data presented in this research confirm that the addition of 1% MC+2% $CaCl_2$ into MTA does not deleteriously alter any of the parent cement's physical properties (marginal leakage, chemical shrinkage, cement solubility, and washout resistance) and that CMMTA performed as well or better than MTA in all of the above tests conducted.

EXAMPLE

Modified MTA

As of 2005, there have been some 150 articles published regarding Mineral Trioxide Aggregate's (MTA) composition, properties, biocompatibility, and indications for use. MTA has become the material of choice for an array of endodontic applications, including vital pulp therapy, apexification, perforation repair, as well as a root-end filling material. Any root-end filling material should have the ability to seal the root canal from bacterial and chemical invasion as well as be biocompatible, prevent periradicular tissue irritation, and ideally favor regeneration of the involved tissues to their preiseased status (1).

MTA has been demonstrated to meet many of the ideal properties of a root-end filling material as described by Gartner and Dom (2). MTA is different from other root-end filling materials currently in use, (Super-EBA, IRM, Amalgam, and composite resin-based materials). Both in vitro and in vivo studies have consistently demonstrated this material to be equal or superior in terms of its biocompatibility (3-9), marginal adaptation (10) and sealing abilities, (11-13), even in the presence of blood and moisture (14).

MTA is a chemical mixture of three powder ingredients: Portland cement (75%), bismuth oxide (20%), and gypsum (5%) (15). These powders consists of fine trioxides and other hydrophilic particles, that upon mixing with sterile water, results in a wet, sandy consistency that sets in the presence of moisture in approximately 165 minutes. Hydration of the powder results in the formation of a colloidal gel with an initial setting pH of 10.2, which increases to 12.5 after 180 minutes. An elemental analysis of MTA revealed an overall composition of MTA as 58.9% Ca, 20.1% Bi, 9.4% Si, 2.1% Al, 2.7% S, 4.4% Fe, with trace amounts of Cr, Ni, and Pb (16).

The unique composition of MTA often makes it hard to use, especially in regions with difficult access. According to Lee (17), MTA is a difficult material to handle due to its granular consistency, slow setting time, and initial looseness. Once the mixture starts to dry, it loses its cohesiveness and becomes unmanageable. Delivery of MTA has focused mainly on carrier and syringable-type devices to simplify placement of the material, however, each still has its own set of problems. The devices can become easily clogged and can be difficult to use due to location and access of the surgical site.

Recent modifications to MTA has been studied and shown to improve the handling characteristics (18). 1% methylcellulose (MC) was added as an anti-washout additive to enhance handling characteristics and provide a more cohesive user-friendly material. This additive does have drawbacks, including decreased compressive strength due to voids entrapped in the cement and longer setting times. To offset these drawbacks, 2% $CaCl_2$ was incorporated as an accelerator to decrease the setting time. The inventors observed that the compressive strength with the additives was not significantly affected compared to MTA at 24 hours and 3 weeks (Table 1) while setting time of MTA with the additives was significantly shorter than the MTA control (Table 2).

TABLE 1

| Compressive strength | 24 hrs | 3 wks |
|---|---|---|
| 1% MC + 2% $CaCl_2$ in MTA | 25.5 ± 4 MPa | 29.1 ± 6.4 MPa |
| MTA (control) | 26.4 ± 6 MPa | 30.4 ± 12.8 MPa. |

TABLE 2

| Setting time | Minutes |
|---|---|
| 1% MC + 2% $CaCl_2$ in MTA | 57 ± 3 |
| MTA (control) | 202 ± 3 |

Materials and Methods—All chemically modified MTA (CMMTA) samples were prepared as described by Ber (18). Briefly, $CaCl_2$ (PCCA, Houston, Tex.) equal to 2% of the sample weight was added to distilled water and mixed into solution. Half of the solution was placed on a hot plate were the temperature of the solution was raised to 80° C. 1% MC (Sigma, St. Louis, Mo.) was added to the warmed solution and stirred to wet the particles. The remainder of the room temperature solution was added and then stirred until all of the powder was in solution. It was then stored at 0° C. for 20 minutes to allow for the mixture to thicken. The solution was then mechanically stirred for 30 minutes to create a homogenous gel. This solution was then added to MTA at a 0.33 water/cement ratio generate a chemically modified MTA cement. All conventional MTA samples were mixed with distilled water according to manufacturer's instructions, using a powder to water ratio of 3:1.

Dye Leakage—Forty-one extracted, human, single-rooted maxillary incisors were collected and stored in 10% formalin. The clinical crowns were decoronated at the cementoenamel junction (CEJ) with a #557 carbide bur in a highspeed handpiece with water coolant. Working length was determined by subtracting 0.5 mm from the length at which a #10 K file exited the apical foramen. Teeth were prepared using rotary instrumentation to a master apical file (IAF) size 40/04 with nickel-titanium (NiTi) ProFile (Tulsa Dental Products, Tulsa, Okla.) instruments via modified crown-down technique in conjunction with RC Prep (Premier, King of Prussia, Pa.) and 5.25% $NaOCl^-$ (Clorox; Clorox Co., Oakland Calif.). The canals were dried with paper points and samples were obturated immediately with Roth Root Canal Cement 801 Elite grade (Roth International Ltd., Chicago, Ill.) and thermoplasticized gutta-percha utilizing an Obtura II (Obtura/Spartan USA, Fenton, Mo.) unit set at 200° C. and expressed in one continuous movement. Canals were then compacted with an S Kondensor plugger (Obtura/Spartan USA, Fenton, Mo.) and coronal access openings sealed with IRM (ID Caulk, Milford, Del.).

All roots were then stored at 37° C. and 100% humidity for 1 week. Apical root resections were performed on all roots by removing 3 mm of each apex at 90 degrees to the long axis of the tooth with a #169 fissure bur using a highspeed handpiece with water coolant. A 3 mm root-end cavity preparation was performed using ultrasonics (Spartan USA, Fenton, Mo.) and KIS tips (Obtura/Spartan USA, Fenton, Mo.) under surgical microscope (Global Surgical Corp., St. Louis, Mo.) at 9.times. magnification. Two coats of nail polish were applied to the entire surface of each root except where the root-end filling was to be placed.

Teeth were randomly assigned to two groups of 15 roots each. Group 1 was retrofilled with MTA (PROROOT, Dentsply Tulsa Dental, Tulsa, Okla.). Group 2 with chemically modified MTA, (1% MC+2% $CaCl_2$ in MTA). An additional 5 roots (Group 3) were filled with high copper amalgam (Tytin Amalgam, Kerr Mfg. Co., Romulus, Mich.) without cavity varnish. Each material was condensed into their respective preparation sites using an S Kondensor plugger. Three instrumented roots with retrograde preparations and no root-end fillings served as positive controls while three roots were instrumented and obturated with gutta-percha and sealer. Entire root surfaces covered with two coats of nail polish were used as negative controls.

All roots were then stored in 1% methylene blue for 72 hours. The roots were rinsed with distilled water and nail polish removed. Teeth were sectioned buccolingually using a 169 tapered fissure bur in a highspeed handpiece and fractured using a Woodson instrument. Dye penetration was evaluated under surgical microscope (Global Surgical Corp., St. Louis, Mo.) at 9× magnification.

Figure 1:
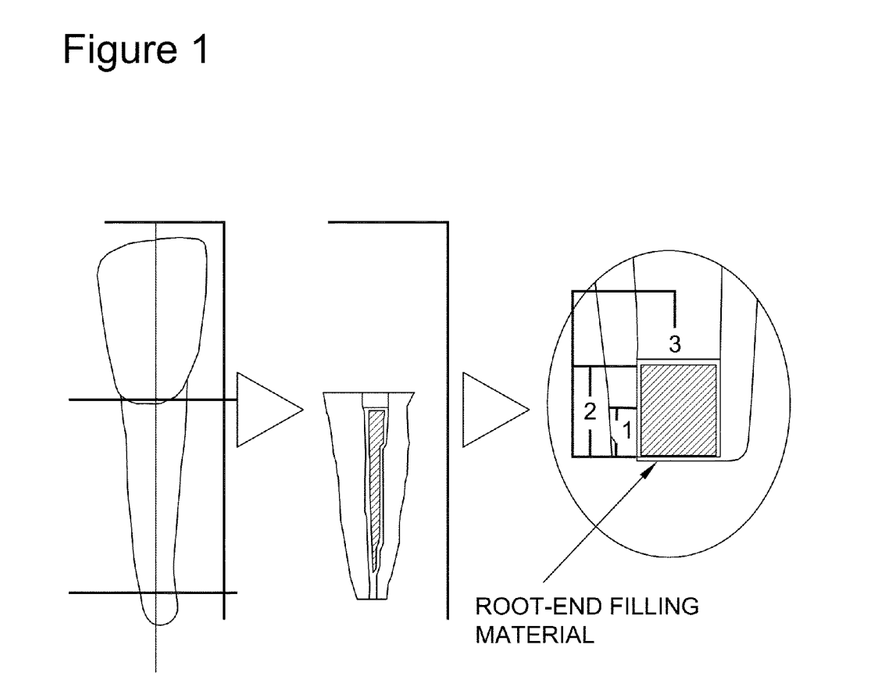
FIG. 1. Root-end filling diagrams and evaluation scores: which 0=no dye penetration observed, 1=dye penetration observed up to ½ of the cavity depth, 2=dye penetration observed between ½ but not beyond root-end filling material placement, 3=dye penetration observed beyond the filling material and into the canal system.

The presence of dye penetration through the material/dentin interface was scored on a four-point scale as shown in FIG. 1, in which 0=no dye penetration observed, 1=dye penetration observed up to 1 of the root-end filling material, 2=dye penetration observed between ½ but not beyond the root-end filling material, 3=dye penetration observed beyond the root-end filling material and into the canal system. Results were recorded and submitted to non-parametric Kruskal-Wallis and Mann-Whitney U-tests.

Figure 2:
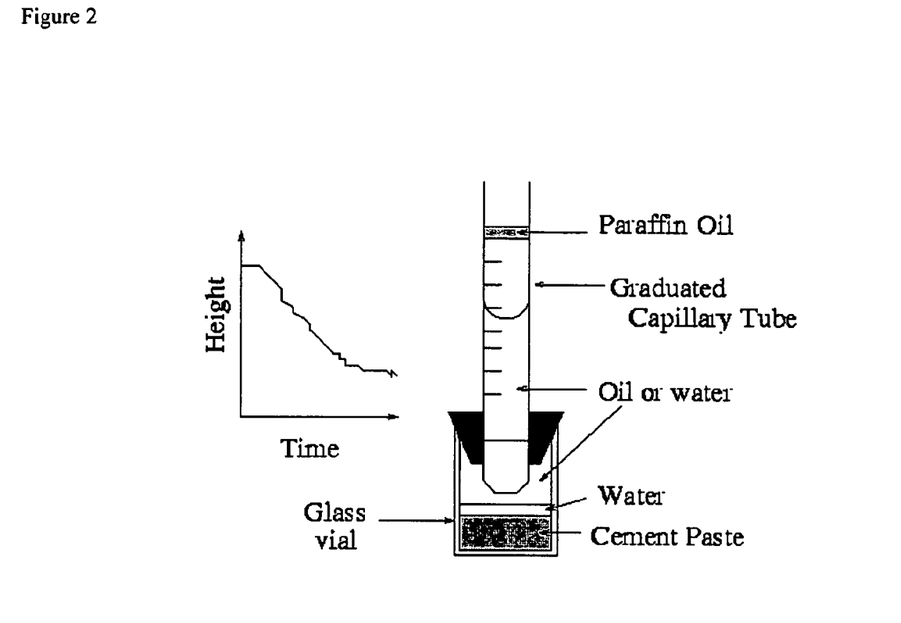
FIG. 2. depicts the chemical shrinkage apparatus.

Chemical Shrinkage—The chemical shrinkage methodology was based on the original work performed by Geiker (19). Modification to Geiker's original work is currently under proposal as the protocol designated to determine chemical shrinkage of Portland cement for the cement industry, (ASTMCXXXX Test Method for Chemical Shrinkage of Hydraulic Cement Paste) (20). All cement pastes were prepared in accordance to manufacturer's instructions at a 0.33 water/cement ratio for groups 1-6 (Group 1=PC/$H_2O$, Group 2=CMMTA, Group 3=MTA/$H_2O$, Group 4=2% $CaCl_2$ in MTA, Group 5=2% $CaCl_2$ in Portland cement, and Group 6=1% MC+2% $CaCl_2$ in Portland cement). The mass of each empty glass vial (diameter=2.5 cm and height=6 cm) was determined to the nearest 0.01 g. Ten grams of cement paste was placed in the bottom of each vial using a vibrating table to achieve a paste height between 5 mm and 10 mm in the vial. Mass of the glass vial was determined with the consolidated cement paste to the nearest 0.0001 g. The remainder of the glass vial was then filled to the top with de-aerated water and sealed with a rubber stopper encasing a pipette graduated in 0.01 ml increments. The respective graduated pipette was then filled to the top with de-aerated water with the addition of 1-2 drops of hydraulic oil to minimize the evaporative process over the 1-week timeframe (FIG. 2). Mass of the vial+capillary tube filled with water and cement paste was immediately determined to the nearest 0.0001 g. The vial was then transferred and placed in a constant temperature water bath of 23.0±0.5° C. At 30 minutes ($T_{30m}$), the glass vial was then removed from the water bath, wiped dry, capillary tube filled to excess with de-aerated water, and mass determined to the nearest 0.0001 g. Additional weight measurements were taken at hourly intervals for the first 8 hours ($T_{1h}$-$T_{8h}$) followed by additional measurements at 24 hours ($T_{24h}$) and 1 week ($T_{168h}$) respectively. Calculation of the mass sample was determined as follows:

The mass of cement powder in the vial is given by:

$$M_{cement} = \frac{(M_{vial+paste} - M_{vialempty})/}{(1.0 + w/c)}$$

$M_{cement}$=mass of cement in the vial (g)
$M_{vial+paste}$=mass of the glass vial with the added cement paste (g)
$M_{vialempty}$=mass of the empty vial (g)
w/c=water-cement ratio by mass of the prepared paste (0.33)

Once the mass of the cement was calculated, this weight in grams was incorporated into the following formula to determine the chemical shrinkage per unit mass at the specific time interval.

The chemical shrinkage per unit mass of cement at time t is computed as:

$CS(t) = ([M(t)-M(30 \text{ min})]/M \text{ cement})/\rho W$

CS(t)=chemical shrinkage at time t (mL/g cement)
M(t)=mass of filled density bottle at time t (g)
$\rho W$=density of water (mL/g) (0.99754 at 23° C.)
M(30 min)=Mass of cement paste at $T_{30m}$ To briefly summarize, two 10 gram specimens were run for each cement group (Group 1=PC/H$_2$O, Group 2=CMMTA, Group 3=MTA/H$_2$O, Group 4=2% CaCl$_2$ in MTA, Group 5=2% CaCl$_2$ in Portland cement and Group 6=1% MC+2% CaCl$_2$ in PC) at a 0.33 water/cement ratio. Weight measurements (0.0001 g) were taken from the shrinkage apparatus initially at 30 minutes ($T_{30m}$) followed by hourly intervals for the first 8 hours ($T_{1h}$-$T_{8h}$). Subsequent weighing of samples were taken at 24 hours ($T_{24h}$) and 1 week ($T_{168h}$) respectively with the resulting average of each group being reported and statistically examined for differences in chemical shrinkage per unit mass between groups at the aforementioned specified time intervals ($T_{1h}$, $T_{2h}$, $T_{3h}$, $T_{24h}$, and $T_{168h}$).

Solubility—Degree of solubility of the test samples was determined by the modified method of ADA/ANSI specification #30 (21) as performed by Torabinejad et al. (22). Briefly, the materials were prepared in accordance to manufacturer's recommendations. Individual MTA and CMMTA samples were hand-mixed and transferred into a small disc approximately 20 mm×1.5 mm by use of a plastic former and two glass slabs. Mixing and weighing of the samples were performed by a single operator at 23.0±2° C. and a relative humidity of 50±5%. 6 discs of MTA and 8 discs of CMMTA were prepared and tested. Following fabrication, discs were placed in 100% humidity for 21 hours. Discs were removed and stored individually in glass jars containing 50 ml of distilled water at 37° C. The specimens were then desiccated for 1 hour at 37° C. Individual discs were weighed to the nearest 0.0001 g and placed back into their respective glass jars. The water in glass jars were neither changed nor added during the test periods. Desiccation and weighing of samples were performed at: 1 day ($T_1$), 7 days ($T_7$) and at 21 days ($T_{21}$). Mean weights of the specimens were recorded and submitted to non-parametric Kruskal-Wallis and Mann-Whitney U-tests to determine statistical differences between weights of the test materials at different time intervals.

Figure 3:
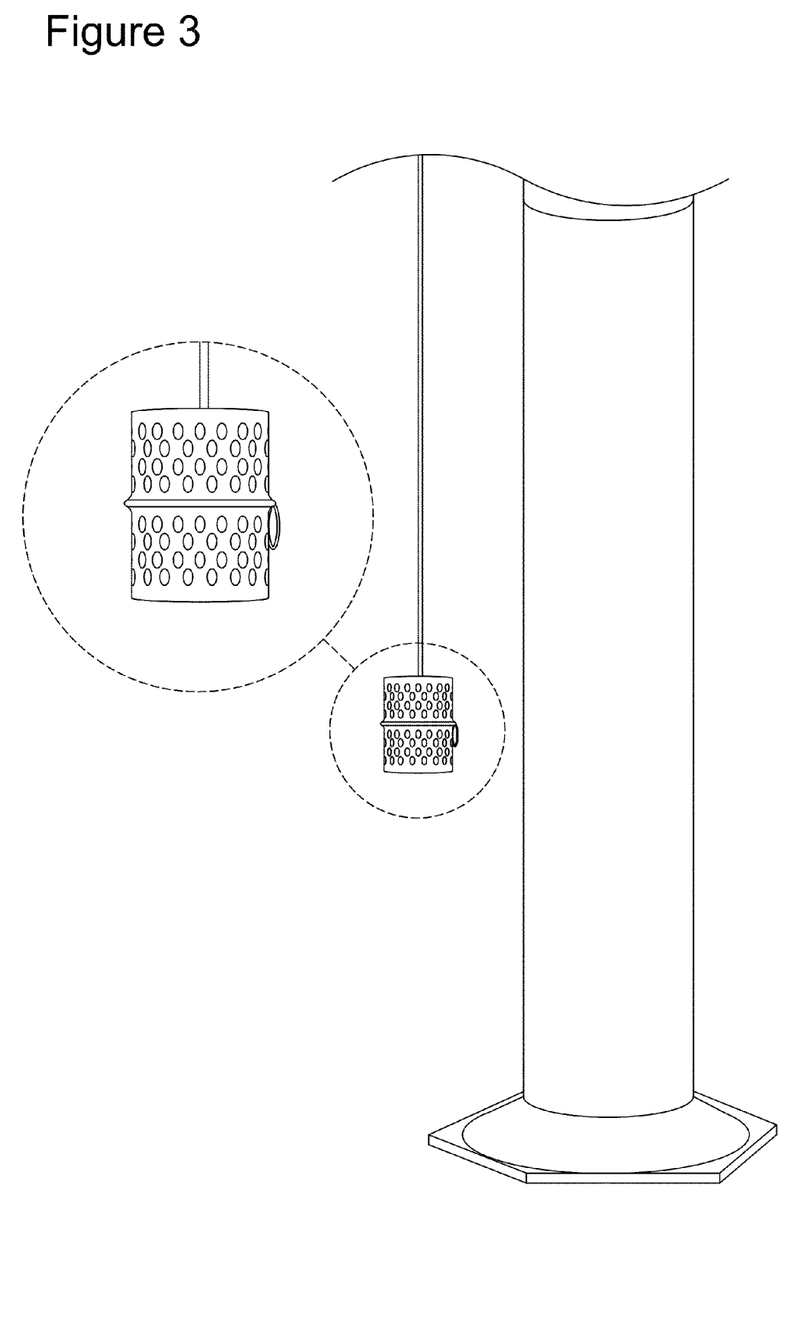
FIG. 3. depicts the receiving container and washout apparatus.
Figure 4:
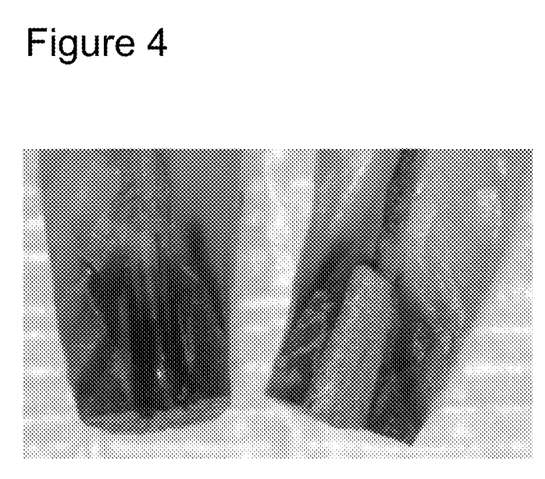
FIG. 4 depicts methylene blue penetration beyond the material dentin interface for amalgam.

Dispersion Resistance/Washout—The percentage of cement washout of the test samples was determined by a modified method based on concrete standard test (CRD-C 61-89A) (24). The receiving container and washout apparatus is shown in FIG. 3. Briefly, two representative 10 gram samples from each group (Group1=Portland cement, Group2=MTA, Group3=CMMTA) were prepared in accordance to manufacturer's instructions at a 0.33 water/cement ratio. Each sample was hand-mixed and placed into a separate receiving container. The cement mixture was tamped down with the handle of a cement spatula 10-15 times to allow the cement to adhere to the walls of the container. Extruded cement was removed from the outside of the receiving container allowing the mass of the cement and container to be obtained and recorded to the nearest 0.0001 g ($M_i$) Immediately following weight measurement, the receiving container with cement sample was allowed to freely fall through the H$_2$O to the bottom of a 1000 ml graduated cylinder and sit for 15 seconds. The receiving container was then slowly raised to the top of the graduated cylinder in 5±1 seconds, allowed to drain for 2 minutes, air dried carefully to remove excess H$_2$O but not disrupt the cement, and weighed to the nearest 0.0001 g. Mass of the cement remaining in the receiving container was recorded as $M_f$. Repeated testing was performed three times on the same cement sample, determining a new $M_f$ each time. The $M_f$ after the final sequence was then calculated as the cumulative loss in mass qualifying as the percent washout of the cement (D) demonstrated below.

Figure 5:
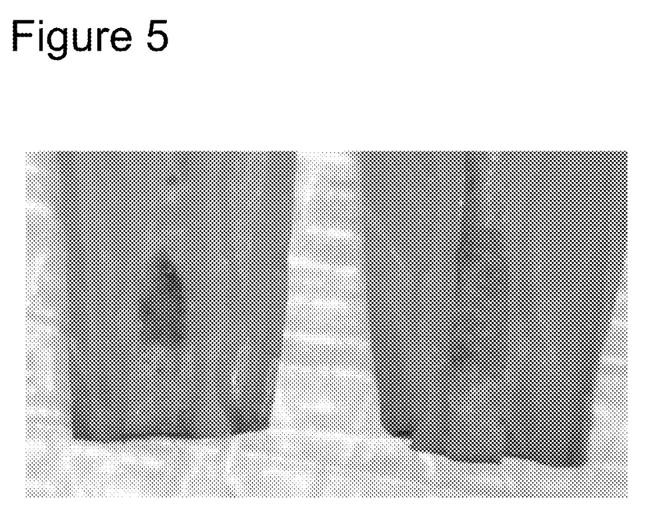
FIG. 5 shows no methylene blue penetration noted for MTA.
Figure 6:
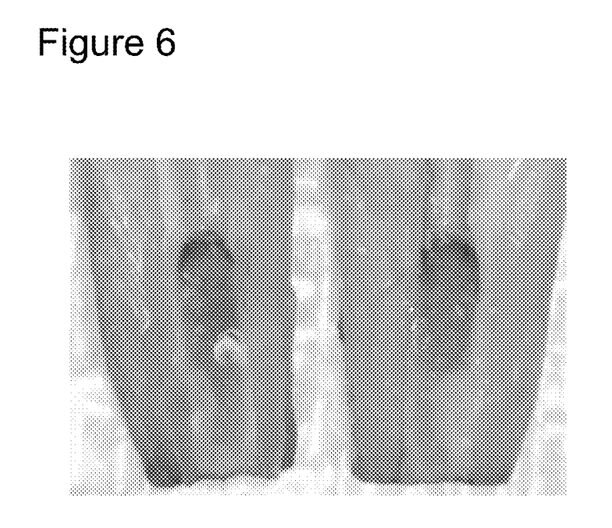
FIG. 6 shows no methylene blue penetration noted for CMMTA.
Figure 7:
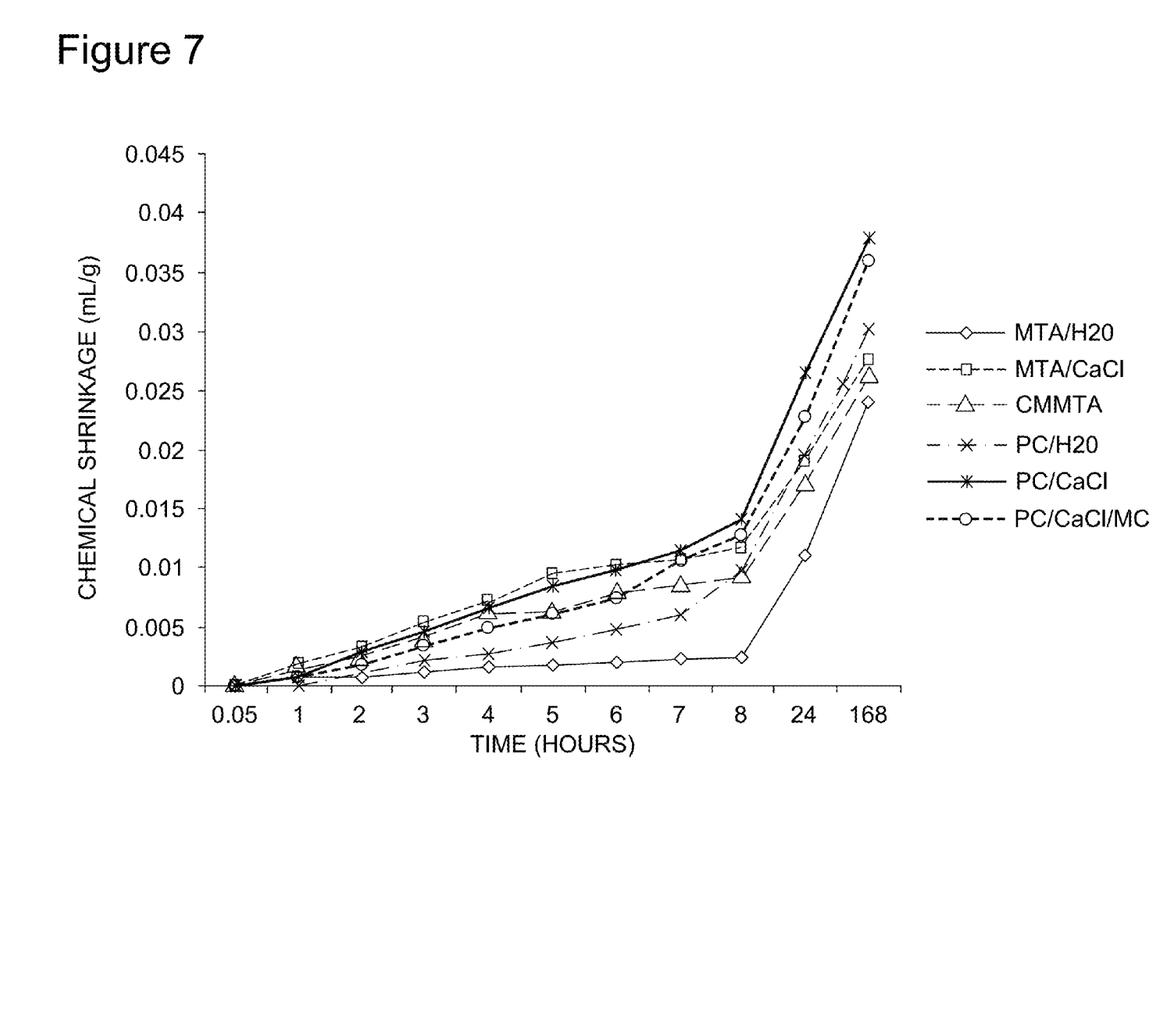
FIG. 7 shows the graph illustrating the chemical shrinkage over 168 hours for samples 1 through 6.

The washout of the cement is computed as: D=($M_i$-$M_f$/$M_i$) 100
D=washout %
$M_i$=mass of sample before initial test
$M_f$=mass of sample after each test Results Results Dye Leakage—Microleakage results of all groups are presented in Table 1. Results from group 1 (MTA) showed that 14 of 15 samples (93%) showed an evaluation score of 0 (no leakage) (FIG. 5). From group 2 (CMMTA), 100% of the specimens displayed an evaluation score of 0 (no leakage) (FIG. 6). In contrast, 100% of the samples from group 3 (amalgam) displayed an evaluation score of 3 (dye penetration throughout the entire canal). The Kruskal-Wallis test was used to compare differences between all groups. This test revealed a significant difference between the groups (P<0.05). When examining differences within groups, the Mann-Whitney U-test showed that leakage observed in Group 1 (MTA) was significantly less (P<0.05) than Group 3 (amalgam). Likewise, Group 2 (CMMTA) displayed significantly less leakage (P<0.05) than Group 3. There was no significant difference noted between Groups 1 (MTA) and 2 (CMMTA) (P<0.05). Positive control samples showed dye leakage throughout the entire canal system, while the negative control samples displayed no signs of dye penetration.

TABLE 3

Results for root-end filling materials.

| Material | No. of Samples | Evaluation Scores | | | |
|---|---|---|---|---|---|
| | | 0 | 1 | 2 | 3 |
| MTA/H$_2$O (Group 1) | 15 | 14 | 0 | 0 | 1 |
| CMMTA (Group 2) | 15 | 15 | 0 | 0 | 0 |
| Amalgam (Group 3) | 5 | 0 | 0 | 0 | 5 |

TABLE 3-continued

Results for root-end filling materials.

| Material | No. of Samples | Evaluation Scores | | | |
|---|---|---|---|---|---|
| | | 0 | 1 | 2 | 3 |
| Positive control† | 3 | 0 | 0 | 0 | 3 |
| Negative control‡ | 3 | 3 | 0 | 0 | 0 |

†Instrumented roots obturated with gutta-percha and sealer; retrograde preparations with no root-end fillings.
‡Instrumented roots obturated with gutta-percha and sealer; entire root surfaces covered with two coats of nail polish.

Chemical Shrinkage—Results from the Kruskal-Wallis test confirmed our rationale and revealed that there was no significant difference noted between groups 1-6 ($P<0.05$). Furthermore, statistical analysis employed with Median tests to compare groups at the designated time intervals ($T_{1h}$, $T_{2h}$, $T_{3h}$, $T_{24h}$, and $T_{168h}$) were unable to show a statistically significant difference in mean chemical shrinkage between the specimens at the previously mentioned time frames ($P<0.05$).

In this experiment, we were interested in the amount of shrinkage that would occur from time $T_{30m}$ to time intervals $T_{1h}$, $T_{2h}$, $T_{3h}$, $T_{24h}$, and $T_{168h}$. Reasoning for these time-frames was that the recommended setting time for MTA is 165 minutes (22). Thus, it is expected that the majority of hydration would be occurring during the initial three hours for MTA and therefore, chemical shrinkage of the cement would be anticipated to be at its greatest. ASTM guidelines for this experiment require hourly measurements for the first 8 hours, a 24 hour reading, and finally at 1 week.

Graph illustrating chemical shrinkage over 8 hours for samples 1-6.

Solubility—The mean weights (g) of the specimens and standard deviation for each test material at various time intervals ($T_{1h}$, $T_{7h}$, $T_{21h}$) are shown in Tables 2 and 3.

TABLE 4

Chemically Modified MTA Solubility Results

| | CMMTA | | | | |
|---|---|---|---|---|---|
| | Wo (Initial weight) | $T_1$ | $T_7$ | $T_{21}$ | Total Change in Mass ($T_0 - T_{21}$) |
| Sample 1 | 0.8925 g | 0.8991 g | 0.9009 g | 0.9075 g | (+)1.68% |
| Sample 2 | 0.9479 g | 0.9528 g | 0.9553 g | 0.9640 g | (+)1.69% |
| Sample 3 | 0.9727 g | 0.9888 g | 0.9899 g | 0.9966 g | (+)1.66% |
| Sample 4 | 0.7681 g | 0.7759 g | 0.7730 g | 0.7756 g | (+)2.46% |
| Sample 5 | 0.9800 g | 0.9720 g | 0.9861 g | 0.9850 g | (+)0.51% |
| Sample 6 | 0.8814 g | 0.8819 g | 0.8896 g | 0.8857 g | (+)0.49% |
| Sample 7 | 0.8791 g | 0.8771 g | 0.8961 g | 0.8879 g | (+)1.00% |
| Sample 8 | 1.0042 g | 0.9968 g | 1.0130 g | 1.0066 g | (+)0.24% |
| Mean wt. | 0.9157 g ± 0.1476 | 0.9181 g ± 0.1422 | 0.9255 g ± 0.1499 | 0.9261 ± 0.1505 | (+)1.14% |

†positive change in mass = +
‡negative change in mas = −

TABLE 5

MTA Solubility Results

| | MTA | | | | |
|---|---|---|---|---|---|
| | Wo (Initial weight) | $T_1$ | $T_7$ | $T_{21}$ | Total Change in Mass ($T_0 - T_{21}$) |
| Sample 1 | 0.8715 g | 0.8611 g | 0.8797 g | 0.8807 g | (+)1.04% |
| Sample 2 | 0.7351 g | 0.7269 g | 0.7467 g | 0.7515 g | (+)2.18% |
| Sample 3 | 0.8607 g | 0.8516 g | 0.8716 g | 0.8773 g | (+)1.66% |
| Sample 4 | 0.9702 g | 0.9569 g | 0.9602 g | 0.9646 g | (−)0.58% |
| Sample 5 | 0.9813 g | 0.9579 g | 0.9578 g | 0.9759 g | (−)0.55% |
| Sample 6 | 0.8139 g | 0.7920 g | 0.7985 g | 0.8128 g | (−)0.135% |
| Mean wt. | 0.8721 g ± 0.1370 | 0.8577 g ± 0.1308 | 0.8686 g ± 0.1219 | 0.8771 g ± 0.1256 | (−)0.57% |

†positive change in mass = +
‡negative change in mas = −

The change in mass for each of the samples revealed that there was a tendency for a positive gain in total mass (+0.024%–+2.46%) with a mean gain of 1.14% over the 21 day period for CMMTA samples. Likewise, half of the MTA samples (1-3) revealed a positive change in mass (+1.04%–+2.18%) while samples 4-6 showed a negative change in mass (−0.135%––0.58%) with an overall mean gain in mass of 0.57% over the 21 day period for the MTA samples. When examining differences between the two groups, the Mann-Whitney U-test displayed no significant differences between MTA and CMMTA in solubility ($P<0.05$). Furthermore, statistical analysis with the Wilcoxon signed ranks test was unable to show a statistical significant difference when the mean weight of the specimens were compared at different time intervals ($T_{1h}$, $T_{7h}$, $T_{21h}$) ($P<0.05$).

Dispersion Resistance/Washout—Weights (g) of each test group with corresponding repeated measures on washout for Portland cement, MTA, and CMMTA is shown in Tables 4-6 respectively. Results from the Friedman test used to analyze the amount of cumulative washout revealed a significant difference observed between groups ($P<0.05$). However, due to the small sample size, Post Hoc analysis (Median test) was unable to identify significant differences within groups.

TABLE 6

Washout Results for Portland Cement

| | Group 1 (Portland cement) | | | | |
|---|---|---|---|---|---|
| | Mi (Initial weight) | Mf(1) | Mf(2) | Mf(3) | Cumulative Percent Washout |
| Test #1 | 21.3368 g | 20.9374 g | 20.8175 g | 20.7019 g | (−)2.9756% |
| Test #2 | 21.9530 g | 21.5350 g | 21.5632 g | 21.4968 g | (−)2.0781% |
| Mean | 21.6449 g | 21.2362 g | 21.1904 g | 21.5994 g | (−)2.5269% |

†positive change in mass = +
‡negative change in mas = −

TABLE 7

Washout Results for MTA

Group 2 (MTA)

| | Mi (Initial weight) | Mf(1) | Mf(2) | Mf(3) | Cumulative Percent Washout |
|---|---|---|---|---|---|
| Test #1 | 20.9886 g | 20.4855 g | 20.4103 g | 20.2767 g | (−)3.3918% |
| Test #2 | 21.4967 g | 20.9457 g | 20.7365 g | 20.6874 g | (−)3.7647% |
| Mean | 21.2427 g | 20.7156 g | 20.5734 g | 20.4821 g | (−)3.5783% |

†positive change in mass = +
‡negative change in mas = −

TABLE 8

Washout Results for Chemically Modified MTA

Group 1 (CMMTA)

| | Mi (Initial weight) | Mf(1) | Mf(2) | Mf(3) | Cumulative Percent Washout |
|---|---|---|---|---|---|
| Test #1 | 21.6637 g | 21.8742 g | 22.0083 g | 22.0091 g | (−)1.5944% |
| Test #2 | 22.0066 g | 22.3133 g | 22.2567 g | 22.2500 g | (−)1.1060% |
| Mean | 21.8352 g | 22.0938 g | 22.1325 g | 22.1296 g | (−)1.3502% |

†positive change in mass = +
‡negative change in mas = −

Dye Leakage—An apicoectomy followed by a root-end filling material is a common endodontic procedure used to rectify recalcitrant periapical pathosis in teeth where orthograde endodontic therapy has failed and nonsurgical treatment is not an option. One of the properties of an ideal root-end filling material is the ability to seal the root canal system (2). Dye leakage studies are a quick an effective method to evaluate the sealing ability of root-end filling materials (22). In 1989, Kersten and Moorer determined the leakage of methylene blue to be comparable to that of a small bacterial metabolic product of similar molecular size. Thus, when a filling material does not allow the penetration of small molecules such as methylene blue, it has the potential to prevent leakage of larger substances such as bacteria and their by-products (24). Under the parameters of this study, leakage was quantified with the use of a Likert four-point scale in which 0=no dye penetration observed, 1=dye penetration observed up to 1 of the cavity depth, 2=dye penetration observed between ½ but not beyond root-end filling material placement, and 3=dye penetration observed beyond the filling material and into the canal system. Thus, greater disparity from a score of zero directly reflects the ability of the root-end filling to adequately seal the dentin/material interface. Graphical representation of leakage scores obtained over 72 hours is presented in Table 1. From this table, we were able to conclude that the greatest disparity occurred between amalgam and CMMTA groups. A similar contrast was also evident between the MTA and amalgam groups. However, there was no significant difference noted in leakage between MTA and CMMTA groups.

Our results indicate that the CMMTA (1% methylcellulose+2% $CaCl_2$ in MTA) was comparable to the unaltered MTA (MTA/$H_2O$) in preventing dye penetration beyond the extent of the material. Therefore, the additives placed into MTA had no significant effect on its sealing properties. In fact, the chemically modified MTA showed no evidence of leakage in all 15 specimens.

Chemical Shrinkage—Numerous properties of cementitious materials are controlled by their initial hydration rate (early-age strength development, heat release, and crack resistance). A direct method for analysis of the cement's initial hydration rate is by quantifying the chemical shrinkage of the cement paste during its hydration. As cement hydrates, the hydration products occupy less volume than the initial reacting materials (cement and water). As a result of this volume change, a hydrating cement paste will absorb water, if available from its immediate surroundings. At early times this water absorption is in direct proportion to the amount of hydration that has occurred (25).

It has been generally considered that a potential root-end filling material should set as soon as it is placed in a root-end cavity without significant shrinkage. This would allow for dimensional stability of the material after placement and less time for an unset material to be in contact with periapical tissues. The incorporation of 1% methylcellulose+2% $CaCl_2$ into MTA by Ber. (18) has demonstrated to show promise to rectify some of MTA's potential shortcomings as a root-end filling material (long setting time and poor handling characteristics). A detrimental effect of calcium chloride is drying shrinkage (26). This study was undertaken to determine if the incorporated additives (namely $CaCl_2$) into MTA significantly affected the chemical shrinkage properties of MTA.

Figure 8:
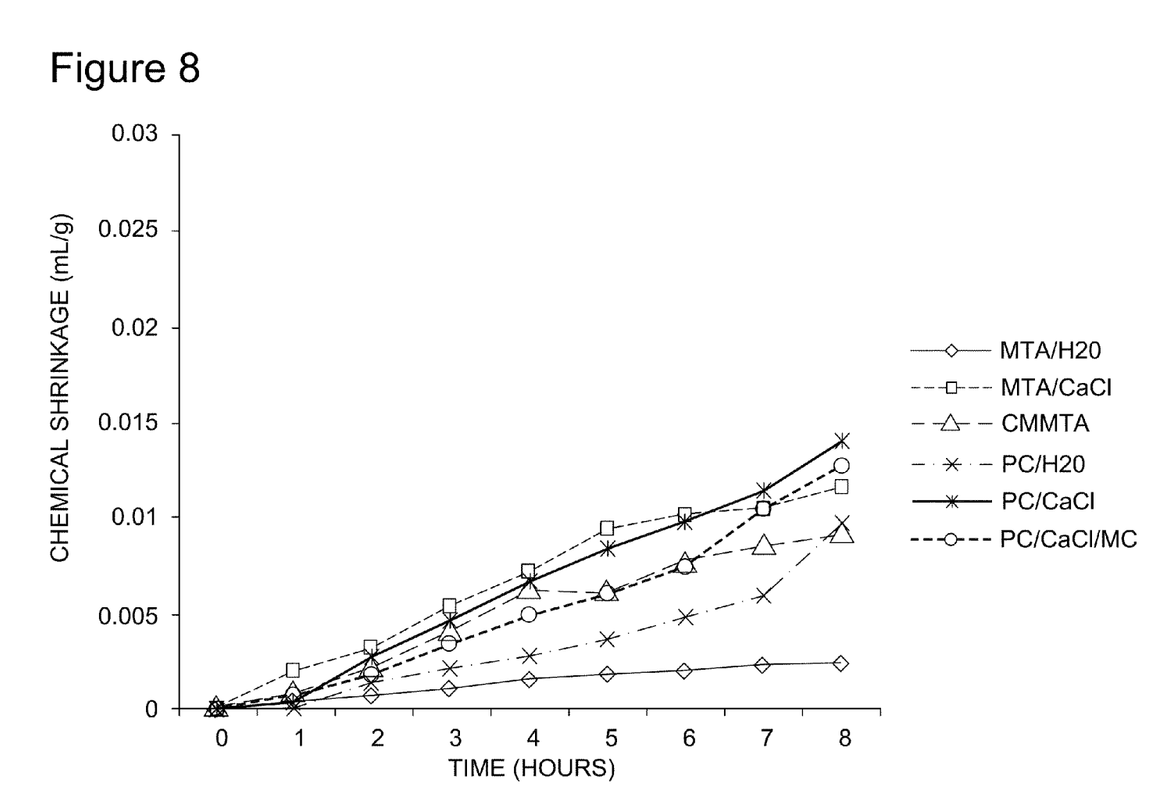
FIG. 8 shows the Graph Illustrating the chemical shrinkage over 8 hours for samples 1 through 6.

Statistical analysis in the mean amount of chemical shrinkage occurring over 1 week (168 hours) for each of the six groups revealed no significant difference between groups at any of the determined time intervals ($P<0.05$). As illustrated in FIG. 8, specimens with the greatest to the least amount of chemical shrinkage displayed over 1 week is represented as follows: Group 5 (2% $CaCl_2$ in PC)>Group 6 (1% MC+2% $CaCl_2$ in PC)>Group 1 (PC/$H_2O$)>Group 4 (2% $CaCl_2$ in MTA)>Group 2 (CMMTA)>Group 3 (MTA/$H_2O$). We expanded the graph to provide a clearer representation of specific trends for each specimen tested relative to early age shrinkage ($T_0$-$T_8$) (FIG. 9). Both figures illustrate a consistent increase in chemical shrinkage for each of the specimens tested over time. Likewise, the addition of 2% calcium chloride revealed a propensity to increase the chemical shrinkage rate. This is expected, since calcium chloride is used as an accelerant to increase the hydration process and provide early-age strength. Nonetheless, statistical analysis was able to demonstrate no significant amount of shrinkage between MTA and CMMTA mean samples.

These results have demonstrated that unique to the dental sector and unlike in the cement industry, small quantities (usually <1 gram) of MTA mixed at a 3:1 w/c ratio placed in intimate contact with periapical tissues which provides 100% humidity within an aqueous environment will enable and maintain saturation of the material and prevent a significant amount of autogenous or drying shrinkage.

Solubility—Root-end filling materials used during periapical surgery are routinely placed in intimate contact with inflamed or infected areas of the periodontium. It is therefore essential that the root-end filling material be given every opportunity to maintain its apical seal and resist dissolution while in the presence of moisture/blood or lowered pH of the involved area. Torabinejad et al. was able to demonstrate that MTA leaked significantly less than amalgam, Super EBA and IRM in the presence of blood, and they observed that the presence or absence of blood had no significant effect on the amount of leakage of the material (27). The rationale for this is that MTA beneficial properties are realized with the added moisture from blood within the surgical site during the hydration process to initiate the initial seal. The literature states the presence of periradicular inflammation may provide an acidic pH of 5.5 and this lowered pH may alter the physical properties of MTA to inhibit setting reactions, affect adhesion, or increase solubility of the material (28). A study performed by Roy et al. was able to demonstrate that the sealing ability of freshly mixed MTA was not affected in an acidic environment (pH 5.0) (29). Conversely, a study performed by Lee et al. was able to make evident that an acid environment of pH 5 adversely affected the physical properties and the hydration behavior of MTA by retarding the dissolution of reactants, ($C_3S$, $C_2S$, and $C_3A$) therefore decreasing the production of Portlandite crystals. Furthermore, SEM and XRD analysis also revealed that the lowered pH had potentiated a decreased hardness value of MTA with dissolution of surface crystals (30).

The inventors observed that the addition of 1% MC and 2% $CaCl_2$ into MTA had no detrimental effects on the material's solubility. Under the parameters used in this example, all specimens were immersed in distilled $H_2O$ for 21 days to provide an adequate timeframe to identify trends in the initial solubility that may affect long-term results. Thus, if the material would show any initial dissolution, there would be a chance that the marginal seal has been disrupted and the potential for leakage to occur.

From the observations, it appears that specimens from both CMMTA and MTA groups showed no or minimal signs of solubility in water over the observation time. In fact, CMMTA and MTA groups both demonstrated mean increases in water absorption over the 21 day period respectively (+1.14% and +0.57%). Our results were somewhat surprising to see a positive change in mean mass for both groups over this timeframe. One may direct this discrepancy to standard measuring error where the specimens were weighed to 0.0001 grams. It is also plausible, methylcellulose, which is traditionally used as a bulking agent in the marketplace, may have potentially absorbed additional water into the cement during the hydration process adding to the higher mean increase in weight of CMMTA. Nonetheless, these results are in agreement with a study performed by Torabinejad, (22) who concluded that MTA, Super-EBA, and amalgam showed no signs of solubility at 21 days.

Clinically, there is no standard method for predictably measuring the manufacturer's recommended 3:1 w/c ratios for MTA. Fridland (31) was able to demonstrate that the degree of solubility in MTA increased as w/c ratio increased. Therefore, the amount of water used in preparing the mix has a direct effect on solubility when the material is in contact with an aqueous environment. This increase in solubility has the potential to affect the long-term seal that can essentially lower the overall success of the endodontic procedure.

Our data is in opposition to a recent study performed by Fridland (32). This long-term study measured solubility over 78 days with varying w/c ratios. The authors concluded that MTA with a 0.33 w/c ratio over 78 days revealed a 24.04% cumulative solubility of the material's initial dry weight. The disparity in solubility results between studies could have resulted from differences in measurement methodology. Fridland et al. calculated solubility according to an amalgamation of ISO 6876 standard (33) and ADA Specification #30 (34). In essence, Fridland et al. used an indirect weight measurement to determine the solubility of MTA. These authors used values from the weighted residues as a percentage of the initial dry weight of the specimens. In contrast, our methodology mirrored a study performed by Torabinejad, (22) who used a modification to ADA Specification #30 using direct measurement of the specimens at the dedicated time intervals.

Dispersion Resistance/Washout—During periapical surgery, root-end filling materials are inevitably exposed to periapical tissues and fluids. This continuous moisture contamination may complicate the placement of an effective seal and place the material at risk to washout of the material. This is particularly relevant for freshly placed MTA because of its lengthy setting time (165 minutes) (22).

MTA seems to have similar vulnerabilities to washout as Portland cement when placed in aqueous environments with prolonged setting times. The cement industry routinely deals with wet conditions (underwater concrete placement) that can potentially affect the properties of the material, not unlike conditions encountered during periapical surgery. For a discussion of how the cement industry addresses problems of wet conditions, see Concrete Construction Engineering Handbook, E. Nawy, ed., New York, CRC Press, 1997; Concrete Construction Handbook, J. Dobrowski, 4th ed., New York, McGraw-Hill, Inc., 1998; and Kosmatka and Panarese, Design and Control of Concrete Mixtures, 13th ed., Portland Cement Association, Skokie, Ill., 1988, all of which are herein incorporated by reference. To address these problems for dental application, an anti-washout mixture (methylcellulose) is added to the cement to facilitate a more cohesive cement. The addition of this additive increases the viscosity of the water used in the mixture, therefore, producing a more thixotropic material to resist washout. Clinically, most of the disintegration of the cement will initially occur during the placement of the material and not once it has set. That is why the addition of this cohesive antiwashout material may inhibit the dispersion of material from the cavity both during placement and as well as the first few hours of setting.

The inventors (18) have adopted the cement industry's solutions to these problems with the addition of 1% methylcellulose+2% $CaCl_2$ in MTA. The inventors evaluated in this example whether the chemically modified MTA has provided added benefits to the parent cement (MTA) in terms of washout resistance. The results obtained in this study landed within the typical performance requirements for allowable washout (<6-12%) of underwater concrete for all of the specimens tested (34). Indeed, our results from the Friedman test used to analyze cumulative washout revealed a significant difference observed between groups ($P<0.05$). When evaluating the data mathematically, one could arrive at a conclusion that the significant difference in mean cumulative washout was between Group 2 (MTA=−3.57%) and Group 3 (CMMTA=+1.34%). As in the solubility study, we would expect to see a negative washout value for CMMTA. The positive cumulative washout for CMMTA could possibly be explained by standard measuring error of the materials during the weight measurement process or inadequate removal of $H_2O$ from the receiving container prior to measurement.

In conclusion, the data presented in this example support our position that the addition of 1% MC+2% $CaCl_2$ into MTA has not deleteriously altered any of the parent cement's additional physical properties (marginal leakage, chemical shrinkage, cement solubility, and washout resistance). On the contrary, the results from the four studies testing the physical properties of CMMTA have concluded: Dye leakage results demonstrated that there was no statistically significant difference noted between CMMTA and MTA samples ($P<0.05$). In addition, we were able to demonstrate significantly less leakage between the CMMTA and MTA groups compared to amalgam ($P<0.05$). Chemical shrinkage results reported no statistically significant difference noted between any of the groups at any of the designated timeframes ($T_1$, $T_2$, $T_3$, $T_{24}$, $T_w$). More importantly, we were able to show no statistically significant difference in mean chemical shrinkage between CMMTA and MTA samples at any of the designated time intervals of the specimens ($P<0.05$). Cement solubility results revealed no statistically significant difference between CMMTA and MTA groups (P<0.05). Furthermore, we were able to show no significant difference between weights of the test materials at different time intervals. Modified washout tests indicated a significant difference observed between groups 1-3 (P<0.05). Data obtained from the study demonstrated CMMTA as having the most mean cumulative washout resistance while MTA displayed the least cumulative washout resistance. However, there were no significant differences noted between these two groups (P<0.05).

The following references are cited throughout this section using the related parenthetical numbering system. The references are incorporated herein by reference. Applicant reserves the right to challenge the veracity of statements made therein.

1) Sarkar N K, Caicedo R, Ritwik P, Moiseyeva R, Kawashima I. Physicochemical basis of the biologic properties of mineral trioxide aggregate. J Endod. 2005; 31:97-100.
2) Gartner A H, Dorn S O. Advances in endodontic surgery. Dent Clin North Am 1992; 36:357-78.
3) Koh E T, Torabinejad M, Pitt Ford T R, Brady K, McDonald F. Mineral trioxide aggregate stimulates a biological response in human osteoblasts. J Biomed Mater Res. 1997; 37:432-9.
4) Koh E T, McDonald F, Pitt Ford T R, Torabinejad M. Cellular response to Mineral Trioxide Aggregate. J Endod 1998; 24:543-7.
5) Torabinejad M, Hong C U, Pitt Ford T R, Kaiyawasama S P. Tissue reaction to implanted super-EBA and mineral trioxide aggregate in the mandible of guinea pigs: a preliminary report. J Endod 1995; 21:569-71.
6) Torabinejad M, Ford T R, Abedi H R, Kariyawasama S P, Tang H M. Tissue reaction to implanted root-end filling materials in the tibia and mandible of guinea pigs. J Endod 1998; 24:468-71.
7) Pitt Ford T R, Torabinejad M, Abedi H R, Bakland L K, Kariyawasama S P. Using mineral trioxide aggregate as a pulp-capping material. J Am Dent Assoc 1996; 127:1491-4.
8) Osorio R M, Hefti A, Vertucci F J, Shawley A L. Cytotoxicity of endodontic materials. J Endod 1998; 24:91-6.
9) Keiser K, Johnson C C, Tipton D A. Cytotoxicity of mineral trioxide aggregate using human periodontal ligament fibroblasts. J Endod 2000; 26:288-91.
10) Torabinejad M, Rastegar A F, Kettering J D, Pitt Ford T R. Bacterial leakage of mineral trioxide aggregate as a root-end filling material. J Endod 1995; 21:109-12.
11) Wu M K, Kontakiotis E G, Wesselink P R. Long-term seal provided by some root-end filling materials. J Endod. 1998; 24:557-60.
12) Torabinejad M, Watson T F, Pitt Ford T R. Sealing ability of a mineral trioxide aggregate when used as a root end filling material. J Endod. 1993; 19:591-5.
13) Martell B, Chandler N P. Electrical and dye leakage comparison of three root-end restorative materials. Quintessence Int. 2002; 33:30-4.
14) Torabinejad M, Higa R K, McKendry D J, Pitt Ford T R. Dye leakage of four root end filling materials: effects of blood contamination. J Endod 1994; 20:159-63.
15) PROROOT MTA, Product Literature, Dentsply Tulsa Dental, Tulsa, Okla. 74136.
16) Deal B, Wenkus C, Johnson B, Fayad M. Chemical and physical properties of MTA, Portland cement, and a new experimental material, fast-set MTA. J Endod 2002; 28:252.
17) Lee E S. A new mineral trioxide aggregate root-end filling technique. J Endod 2000; 26:764-5.
18) Ber, B S. "Manipulation of Handling Characteristics of MTA," Master's Thesis, Saint Louis University, 2004.
19) M. Geiker, Studies of Portland Cement Hydration: Measurements of Chemical Shrinkage and a Systematic Evaluation of Hydration Curves by Means of the Dispersion Model. Ph. D. Thesis, Technical University of Denmark, 1983.
20) Proposed test method ASTM CXXXX Test method for chemical shrinkage of hydraulic cement paste. ASTM Committee C-1. Subcommittee C01.31 on volume change.
21) ANSI/ADA. Revised American National Standard/American Dental Association Specification No. 30 for dental zinc oxide eugenol cements and zinc oxide noneugenol cement 7.5, 2000.
22) Torabinejad M, Hong C U, McDonald F, Pitt Ford T R. Physical and chemical properties of a new root-end filling material. J Endod 1995; 21:349-53.
23) Proposed test method ASTM CXXXX Test method for chemical shrinkage of hydraulic cement paste. ASTM Committee C-1. Subcommittee C01.31 on volume change.
24) Kersten H W, Moorer W R. Particles and molecules in endodontic leakage. Int Endod J. 1989; 22:118-24.
25) Parrott L. J, Geiker M, Gutteridge W. A., Killoh D., Monitoring Portland cement hydration: comparison of methods. Cement and Concrete Research. 1990; 20:919-926.
26) Kosmatka, Steven H., and Panarese, William C. Design and Control of Concrete Mixtures, 13th ed., PortlandCement Association, Skokie, Ill. 1988.
27) Torabinejad M, Higa R K, McKendry D J, Pitt Ford T R. Dye leakage of four root end filling materials: effects of blood contamination. J Endod 1994; 20:159-63.
28) Malamed S. Chapter 16. In: Local anesthetic considerations in dental specialties: handbook of local anesthesia. 4th edni. St. Louis: Mosby; 1997; p. 232.
29) Roy C O, Jeansonne B G, Gerrets T F. Effect of an acid environment on leakage of root-end filling materials. J Endod 2001; 27:7-8.
30) Lee Y L, Lee B S, Lin F H, Yuni Lin A, Lan W H, Lin C P. Effects of physiological environments on the hydration behavior of mineral trioxide aggregate. Biomaterials. 2004; 25:787-93.
31) Fridland M, Rosado R. Mineral trioxide aggregate (MTA) solubility and porosity with different water-to-powder ratios. J Endod. 2003; 29:814-7.
32) Fridland M, Rosado R. MTA Solubility: A Long Term Study. J Endod. 2005; 31:376-379.
33) International Organization for Standardization. Specification for dental root canal sealing materials. ISO 6876. London: British Standards Institution, 2001.
34) ANSI/ADA. Revised American National Standard/American Dental Association Specification No. 30 for dental zinc oxide eugenol cements and zinc oxide noneugenol cement 7.5, 2000.
35) Department of the Army EC 1110-2-6052. U.S. Army Corps of Engineers CECW-EI Washington, D.C. 20314-1000. 2001; Appendix B-6.

What is claimed is:

1. A dental repair composition consisting of: a mineral trioxide aggregate, a divalent cation halogen salt, and a cellulose polymer selected from the group consisting of methyl cellulose, ethyl cellulose, ethyl methyl cellulose, hydroxyethyl cellulose, hydroxyethyl methyl cellulose, hydroxypropyl cellulose, ethyl hydroxyethyl cellulose, and carboxymethyl cellulose.

2. The dental repair composition of claim 1, wherein the divalent cation halogen salt is selected from the group consisting of calcium chloride, magnesium chloride, sodium chloride, and potassium chloride.

3. The dental repair composition of claim 1, wherein the divalent cation halogen salt is from about 0.1% (w/w) to about 10% (w/w).

4. The dental repair composition of claim 1, wherein the divalent cation halogen salt is about 2% (w/w).

5. The dental repair composition of claim 1, wherein the cellulose polymer is from about 0.1% (w/w) to about 10% (w/w).

6. The dental repair composition of claim 1, wherein the cellulose polymer is about 1% (w/w).

7. The dental repair composition of claim 1 consisting of a setting time of less than 200 minutes.

8. The dental repair composition of claim 1 consisting of a viscosity of from about 50,000,000 centipoise to about 150,000,000 centipoise.

9. The dental repair composition of claim 1 consisting of a compressive strength measured at about 24 hours of from about 20 MPa to about 30 MPa.

10. The dental repair composition of claim 1 consisting of a compressive strength measured at about 3 weeks of from about 22 MPa to about 36 MPa.

11. A dental repair composition prepared by a process comprising:
 preparing a divalent cation halogen salt solution; warming a portion of the divalent cation halogen salt solution to a temperature of between about 60° C. to about 90° C. to prepare a warmed divalent cation halogen salt solution; mixing a cellulose polymer selected from the group consisting of methyl cellulose, ethyl cellulose, ethyl methyl cellulose, hydroxyethyl cellulose, hydroxyethyl methyl cellulose, hydroxypropyl cellulose, ethyl hydroxyethyl cellulose, and carboxymethyl cellulose with the warmed divalent cation halogen salt solution to prepare a warmed divalent cation halogen salt-cellulose polymer solution; mixing a remaining portion of the divalent cation halogen salt solution with the warmed divalent cation halogen salt cellulose polymer solution; cooling warmed divalent cation halogen salt cellulose polymer solution to a temperature of between about 0° C. to about 10° C. to form a gel; mixing the gel with a mineral trioxide aggregate solution to prepare the dental repair composition, wherein the dental repair composition consists of a mineral trioxide aggregate, a divalent halogen salt, and a cellulose polymer selected from the group consisting of methyl cellulose, ethyl cellulose, ethyl methyl cellulose, hydroxyethyl cellulose, hydroxyethyl methyl cellulose, hydroxypropyl cellulose, ethyl hydroxyethyl cellulose, and carboxymethyl cellulose.

12. The dental repair composition of claim 11, wherein the divalent cation halogen salt is selected from the group consisting of calcium chloride, magnesium chloride, sodium chloride, and potassium chloride.

13. The dental repair composition of claim 11, wherein the divalent cation halogen salt is from about 0.1% (w/w) to about 10% (w/w).

14. The dental repair composition of claim 11, wherein the divalent cation halogen salt is about 2% (w/w).

15. The dental repair composition of claim 11, wherein the cellulose polymer is from about 0.1% (w/w) to about 10% (w/w).

16. The dental repair composition of claim 11, wherein the cellulose polymer is about 1% (w/w).

17. A dental repair kit consisting of in a first container a mineral trioxide aggregate, in a second container a divalent cation halogen salt, in a third container a cellulose polymer selected from the group consisting of methyl cellulose, ethyl cellulose, ethyl methyl cellulose, hydroxyethyl cellulose, hydroxyethyl methyl cellulose, hydroxypropyl cellulose, ethyl hydroxyethyl cellulose, and carboxymethyl cellulose; and
 instructions for making a dental repair composition consisting of: a mineral trioxide aggregate, a divalent cation halogen salt, and a cellulose polymer selected from the group consisting of methyl cellulose, ethyl cellulose, ethyl methyl cellulose, hydroxyethyl cellulose, hydroxyethyl methyl cellulose, hydroxypropyl cellulose, ethyl hydroxyethyl cellulose, and carboxymethyl cellulose.

\* \* \* \* \*